(12) United States Patent
Kouno et al.

(10) Patent No.: US 6,489,509 B2
(45) Date of Patent: Dec. 3, 2002

(54) METHODS OF STORING AQUEOUS POTASSIUM SORBATE SOLUTION

(75) Inventors: Mitsuhiro Kouno, Arai (JP); Noboru Kamei, Himeji (JP)

(73) Assignee: Daicel Chemical Industries, Ltd., Osaka (JP)

( * ) Notice: Subject to any disclaimer, the term of this patent is extended or adjusted under 35 U.S.C. 154(b) by 0 days.

(21) Appl. No.: 09/847,320

(22) Filed: May 3, 2001

(65) Prior Publication Data

US 2001/0047109 A1 Nov. 29, 2001

(30) Foreign Application Priority Data

May 29, 2000 (JP) ........................................ 2000-159117

(51) Int. Cl.$^7$ ........................... C07C 57/18; C07C 57/10
(52) U.S. Cl. ........................................ 562/601; 562/598
(58) Field of Search .................................. 562/601, 598

(56) References Cited

U.S. PATENT DOCUMENTS 2,866,819 A  * 12/1958  Montagna et al. .......... 260/526

OTHER PUBLICATIONS

"Oxidation of Sorbic Acid in Aqueous Solution with Oxygen", Lauri Pekkarinen; Pertti Rissanen, Suomen Kemistilehti, vol. 39, issue 3, pp. 50–56 (1966).*

"Mechanism of Oxidation of Sorbic Acid by Molecular Oxygen in Water", Lauri Pekkarinen. Suomen Kemistilehti, vol. 42, issue 3, pp. 147–152 (1969).*

* cited by examiner

*Primary Examiner*—John M. Ford
*Assistant Examiner*—Zachary C. Tucker
(74) *Attorney, Agent, or Firm*—Birch, Stewart, Kolasch & Birch, LLP

(57) ABSTRACT

An aqueous potassium sorbate solution has a dissolved oxygen concentration of not more than 3.0 mg/l. The aqueous potassium sorbate solution can be obtained (i) by degassing an aqueous potassium sorbate solution to thereby control the dissolved oxygen concentration to 3.0 mg/l or less, or (ii) by performing a reaction in a system, in which the oxygen concentrations of the gas phase and of materials to be reacted are reduced, in the production of an aqueous potassium sorbate solution by a reaction of sorbic acid and potassium hydroxide in the presence of water. The resulting aqueous potassium sorbate solution exhibits successively stable hue.

2 Claims, No Drawings

METHODS OF STORING AQUEOUS POTASSIUM SORBATE SOLUTION

BACKGROUND OF THE INVENTION

1. Field of the Invention

The present invention relates to an aqueous potassium sorbate solution exhibiting successively stable hue, a production method and a storing method of the same, and a method of producing potassium sorbate.

2. Description of the Related Art

Sorbic acid and its salts have antiseptic and antimicrobial activities and are substantially nontoxic to the human body in normal concentrations in practical use. These compounds are therefore useful as food additives. Of a variety of known processes for producing sorbic acid, a commercially important pathway is a process of polymerizing crotonaldehyde and ketene to form an intermediate polyester, and decomposing the polyester to yield sorbic acid. Sorbic acid obtained by this technique contains a variety of colored substances and other impurities and is generally subjected to a purification operation such as treatment with activated carbon, distillation or recrystallization, and is then subjected to a neutralization reaction with potassium hydroxide to thereby yield potassium sorbate. The above-prepared potassium sorbate is in an aqueous solution state and is generally further subjected to a drying process to evaporate water to thereby yield powdery potassium sorbate, or is further subjected to a granulation process to thereby yield granular potassium sorbate. In actual use as a food additive, however, potassium sorbate is dissolved again in water and is used as an aqueous solution.

In general, potassium sorbate increases in color and odor over time after its production and is deteriorated in quality. Potassium sorbate in an aqueous solution state particularly strongly has this tendency and is deteriorated in quality in a short time, and the solution itself is colored. A powdery or granular potassium sorbate obtained by drying such a colored aqueous potassium sorbate solution is naturally colored and does never exhibit a recovered hue.

Regarding dried potassium sorbate, a variety of measures to prevent deterioration in quality have been taken and many proposals have been made. Such proposals include, for example, a production method, in which colored substances are removed in the production process to thereby improve hue immediately after production, and a storing method, in which a storage container is sealed with an inert gas or a moisture-impermeable packing material is used. However, each of these techniques is directed to dried potassium sorbate, and no effective solution on potassium sorbate in an aqueous solution state has been proposed. Accordingly, the aqueous potassium sorbate solution must be immediately dried and granulated to yield a dried product in conventional production methods.

SUMMARY OF THE INVENTION

Accordingly, an object of the present invention is to provide an aqueous potassium sorbate solution exhibiting successively stable hue, and methods of producing and storing the aqueous solution.

Another object of the present invention is to provide an aqueous potassium sorbate solution and methods of producing and storing the same, which are useful for obtaining potassium sorbate exhibiting satisfactory and successively stable hue.

A further object of the present invention is to provide a method of producing potassium sorbate exhibiting satisfactory and successively stable hue.

To achieve the above objects, the present inventors focused attention, among a series of production steps for potassium sorbate, on a step for the neutralization of sorbic acid with potassium hydroxide and on the resulting aqueous potassium sorbate solution obtained in this step. They found that there is a link between deterioration of hue and dissolved oxygen contained in an aqueous solution, when potassium sorbate is stored in the state of an aqueous solution. This finding suggested that colored substances are formed by an action of oxygen dissolved in the aqueous solution. Finally, the present inventors found that deterioration of hue during storage as an aqueous solution can be prevented by controlling the dissolved oxygen concentration in the aqueous potassium sorbate solution to a specific range and that this type of aqueous potassium sorbate solution can yield potassium sorbate exhibiting satisfactory and successively stable hue (color).

Specifically, the present invention provides, in an aspect, an aqueous potassium sorbate solution having a dissolved oxygen concentration of 3.0 mg/l or less.

In another aspect, the present invention provides a method of producing an aqueous potassium sorbate solution, which includes the step of degassing an aqueous potassium sorbate solution to thereby control the dissolved oxygen concentration in the aqueous solution to 3.0 mg/l or less.

In a further aspect, the invention provides a method of producing an aqueous potassium sorbate solution, which includes the step of allowing sorbic acid to react with potassium hydroxide in the presence of water. In this method, the reaction is performed in a system in which the oxygen concentrations of a gas phase and of materials to be reacted are reduced to thereby yield an aqueous potassium sorbate solution having a dissolved oxygen concentration of 3.0 mg/l or less.

The invention provides, in yet another aspect, a method of storing an aqueous potassium sorbate solution, which includes the step of storing an aqueous potassium sorbate solution having a dissolved oxygen concentration of 3.0 mg/l or less in such a condition that the oxygen concentration of a gas phase above the liquid level of the aqueous solution is less than that in the atmospheric air.

The invention provides, in another aspect, a method of storing an aqueous potassium sorbate solution, which includes the step of storing an aqueous potassium sorbate solution having a dissolved oxygen concentration of 3.0 mg/l or less in a container composed of an oxygen-impermeable material.

In addition and advantageously, the invention provides a method of producing potassium sorbate, which includes the step of drying an aqueous potassium sorbate solution having a dissolved oxygen concentration of 3.0 mg/l or less to thereby yield a powdery or granular potassium sorbate.

DESCRIPTION OF THE PREFERRED EMBODIMENTS

A feature of an aqueous potassium sorbate solution of the present invention is that the aqueous solution has a dissolved oxygen concentration of 3.0 mg/l or less. If the dissolved oxygen in the aqueous potassium sorbate solution is out of the above-specified range, the aqueous solution markedly becomes colored over time. This is provably because colored substances are formed by action of oxygen contained in the aqueous potassium sorbate solution. In other words, minimized oxygen prevents the formation of colored substances to thereby reduce hue change over time.

The aqueous potassium sorbate solution is obtained by allowing sorbic acid to react with potassium hydroxide in the presence of water. Material sorbic acid is not specifically limited and includes any sorbic acid obtained by a known or conventional method. Sorbic acid is generally produced by, for example, a process in which crotonaldehyde is allowed to react with ketene in the presence of a catalyst such as a zinc salt of fatty acid to yield a polyester, and the polyester is hydrolyzed with an acid or alkali. The above-prepared sorbic acid generally contains a variety of impurities and requires a purification operation to remove the impurities. The purification operation includes, but is not limited to, treatment with activated carbon, distillation, recrystallization, and other known or conventional operations, and combinations of these operations.

Potassium hydroxide for use herein includes any potassium hydroxide which is pursuant to industrial standards and is commercially available, of which an aqueous potassium hydroxide solution is preferred for its easiness in handling. The concentration of such an aqueous potassium hydroxide solution is, for example, from about 45% to about 50% by weight, and preferably from about 49% to about 50% by weight.

A reaction (a neutralization reaction) between sorbic acid and potassium hydroxide is performed in the presence of water. For example, an aqueous slurry of sorbic acid is mixed with an aqueous potassium hydroxide solution to thereby yield potassium sorbate. A reaction temperature is, for example, from about 0° C. to 80° C., and pH of the reaction mixture during reaction is from about 8 to about 13. Upon the completion of reaction, pH is preferably adjusted to about 11. The reaction can be performed in any of a continuous system, semi-batch system and batch system.

The invented aqueous potassium sorbate solution can be obtained, for example, by reducing the dissolved oxygen concentration of the aqueous potassium hydroxide solution and water (water for the preparation of the sorbic acid slurry) for use in the neutralization reaction and the oxygen concentration of a gas phase of the reaction system less than those in normal conditions, in the aforementioned production method. Alternatively, it can be obtained by subjecting an aqueous potassium sorbate solution after the completion of reaction to an operation for removing dissolved oxygen (degassing operation). Any of these techniques can be chosen and employed in the invention.

More specifically, the aqueous potassium sorbate solution having a dissolved oxygen concentration of 3.0 mg/l or less can be obtained by allowing sorbic acid to react with potassium hydroxide under such a condition that the material aqueous potassium hydroxide solution and water are subjected to a degassing operation to thereby reduce the dissolved oxygen concentration to 3.0 mg/l or less and that the oxygen concentration of the gas phase is reduced (10.5% by volume or less, preferably 5% by volume or less, and most preferably 0% by volume) less than that of the atmosphere (air). The reduction of oxygen concentration can be performed by, for example, replacing the gas phase with an inert gas such as nitrogen gas. Alternatively, an aqueous potassium sorbate solution exhibiting successively stable hue which compares favorably with the above-prepared product can be obtained by subjecting an aqueous potassium sorbate solution to a degassing operation immediately after the completion of reaction, without any measure for reducing oxygen during the reaction.

As the technique for removing dissolved oxygen of the aqueous potassium sorbate solution or the material aqueous potassium hydroxide solution or water, any technique can be selected, as far as the resulting dissolved oxygen concentration of the aqueous potassium sorbate solution is ultimately 3.0 mg/l or less. Such techniques include, for example, bubbling of an inert gas such as nitrogen gas into the target liquid, and reduction of pressure of a gas phase above the liquid level. Each of these techniques can be used in combination with an operation for further efficiently removing dissolved oxygen, such as stirring or agitation of the liquid. Each of these techniques can be used alone or in combination, depending on the scale of production to thereby efficiently reduce dissolved oxygen.

Even when the dissolved oxygen concentration in the aqueous potassium sorbate solution is once controlled to 3.0 mg/l or less, the dissolved oxygen concentration returns to that in normal conditions in a short time if it is left in the ambient atmosphere. According to a storing method of the present invention, an aqueous potassium sorbate solution having a dissolved oxygen concentration of 3.0 mg/l or less is stored in such a condition that the oxygen concentration of a gas phase above the liquid level is less than that of the atmosphere. In the storage, the gas phase of a container should preferably have a minimum volume within a range inviting no problem in practical use. Additionally, the gas phase should preferably have an oxygen concentration of half or less (10.5% by volume or less) of that of the normal atmosphere, and particularly preferably 5% by volume or less.

If a storage container is composed of an oxygen-permeable material, oxygen permeates through the container to the aqueous potassium sorbate solution to increase the dissolved oxygen concentration to thereby color the aqueous solution in a long-term storage. According to another storing method of the invention, an aqueous potassium sorbate solution having a dissolved oxygen concentration of 3.0 mg/l or less is stored in a container composed of an oxygen-impermeable material. Such storage containers include, but are not limited to, glass containers, containers made of stainless steel and other metals, and resinous containers having an oxygen barrier coating film. In preferred materials for the container, the components thereof do not solve out into the aqueous potassium sorbate solution.

In preferred storing methods, the dissolved oxygen concentration of the aqueous solution is reduced during or immediately after the reaction between sorbic acid and potassium hydroxide, and contact with oxygen is avoided. Such storing methods are therefore useful to produce an aqueous potassium sorbate solution exhibiting stable hue over the long time.

According to a method of producing potassium sorbate of the present invention, the aforementioned aqueous potassium sorbate solution having a dissolved oxygen concentration of 3.0 mg/l or less is dried to thereby yield a powdery or granular potassium sorbate. Powdering or granulation of the aqueous potassium sorbate solution by drying can be performed by a known or conventional process. For example, granulation processes of potassium sorbate include extrusion granulation, in which the moisture of the powder is controlled with a moisture conditioner, and the powder is extruded; fluidized-bed granulation drying process, in which the aqueous solution is sprayed with hot air to form a fluidized bed, and drying and granulation are concurrently performed; as well as spray drying, tumbling granulation, oscillating granulation, and compression molding.

According to the present invention, the aqueous potassium sorbate solution exhibits markedly low coloring even after a lapse of a long time from the production and can be advantageously used as intact as a food additive for a long-term preservation. Additionally, when the aqueous solution is further subjected to a drying process to yield a dry powder, the aqueous solution can be stored without deterioration of hue and quality even in a process in which the aqueous solution must be left for some time after the completion of reaction due to process limits. Accordingly, the invented methods are greatly significant and useful.

The product potassium sorbate can be used as a preservative for foods such as fish pastes, butters, cheeses, bean pastes, and preserves.

As thus described, the invented aqueous potassium sorbate solution has a dissolved oxygen concentration in a specific range to thereby reduce the oxygen-induced formation of colored substances, and therefore exhibits successively stable hue. The invented method can easily and efficiently produce such an aqueous potassium sorbate solution exhibiting successively stable hue.

According to the invented method of storing an aqueous potassium sorbate solution, an excellent hue quality (color quality) can be maintained over a long time. Additionally, the invented method of producing potassium sorbate can easily produce potassium sorbate exhibiting satisfactory and successively stable hue.

EXAMPLES

The present invention will now be illustrated in further detail with reference to several examples and comparative examples below, which are not intended to limit the scope of the invention.

Example 1

Purified sorbic acid was put into distilled water in a reactor and was stirred to form a slurry, and a 49% by weight aqueous potassium hydroxide solution was added dropwise to the slurry for a neutralization reaction. Sorbic acid and the aqueous potassium hydroxide solution were intermittently supplied to the reactor so that pH of the reaction mixture remained within a range from 8 to 13. Ultimately, 2.22 parts by weight of sorbic acid and 2.27 parts by weight of the aqueous potassium hydroxide solution relative to 1 part of distilled water initially charged were allowed to react for three hours plus. The temperature of the reaction mixture during reaction was held at 25° C., and pH of the reaction mixture on the completion of reaction was adjusted to 11 with a 10% by weight aqueous potassium hydroxide solution.

Nitrogen gas was blown into the above-prepared aqueous potassium sorbate solution with stirring to thereby degas the aqueous solution to a dissolved oxygen concentration of 3.0 mg/l or less. The aqueous potassium sorbate solution had a light transmittance (color valency) of 98.0%, as determined at a wavelength of 430 nm using a spectrophotometer with distilled water as a reference. The thus-prepared aqueous potassium sorbate solution was placed in a glass bottle, and the gas phase thereof having a volume of 5% of the aqueous potassium sorbate solution was purged and replaced with nitrogen gas and the bottle was sealed. The aqueous solution was then stored at room temperature of 20° C. for two months. The resulting aqueous solution had a light transmittance at 430 nm of 95.0% as determined in the same manner as above.

Example 2

An aqueous potassium sorbate solution was obtained in the same manner as in Example 1, except that the distilled water in the reactor and the aqueous potassium hydroxide solution for use in reaction were previously subjected to a degassing operation to a dissolved oxygen concentration of 3.0 mg/l or less, that sorbic acid was allowed to react with potassium hydroxide in the system which had been purged and replaced with nitrogen, and that a degassing operation after the completion of reaction was not performed. This aqueous potassium sorbate solution had a light transmittance (color valency) of 98.5%, as determined at a wavelength of 430 nm using a spectrophotometer with distilled water as a reference. The thus-prepared aqueous potassium sorbate solution was placed in a glass bottle, and the gas phase thereof was purged and replaced with nitrogen gas and the bottle was sealed. The aqueous solution was then stored at room temperature of 20° C. for two months. The resulting aqueous solution had a light transmittance at 430 nm of 95.5% as determined in the same manner as above.

Example 3

The procedure of Example 1 until the pH adjustment on the completion of reaction was repeated to thereby yield an aqueous potassium sorbate solution. This aqueous solution was found to have a light transmittance (color valency) of 98.0%, as determined at a wavelength of 430 nm using a spectrophotometer with distilled water as a reference. Nitrogen gas was blown into the aqueous solution as intact in the reactor (made of stainless steel) with stirring to a dissolved oxygen concentration of 3.0 mg/l or less. The gas phase above the liquid level in the reactor was purged and replaced with nitrogen gas and the reactor was sealed, and the temperature of the liquid in the reactor was increased to 60° C. After a lapse of four days in this condition, the aqueous potassium sorbate solution in the reactor was sampled and was found to have a light transmittance at 430 nm of 96.0%.

Comparative Example 1

The dissolved oxygen concentration of the aqueous potassium sorbate solution obtained after the completion of reaction in the procedure of Example 1 was determined without a degassing operation, and was found to be 7.8 mg/l. This aqueous potassium sorbate solution was found to have a light transmittance (color valency) of 98.0%, as determined at a wavelength of 430 nm using a spectrophotometer with distilled water as a reference. The aqueous solution was stored at room temperature of 20° C. in an atmospheric open system for two months without any degassing operation. The light transmittance at 430 nm of the resulting aqueous solution was determined in the same manner as above and was found to be 58.0%.

Comparative Example 2

The procedure of Example 1 was repeated, except that a storage container made of polypropylene was used and that the gas phase of the storage container was not replaced with nitrogen gas. The resulting aqueous potassium sorbate solution was stored at room temperature of 20° C. for two months and was then found to have a light transmittance at 430 nm of 85. 0%.

Comparative Example 3

The procedure of Example 1 was repeated, except that a storage container made of polypropylene was used. The resulting aqueous potassium sorbate solution was stored at room temperature of 20° C. for two months and was then found to have a light transmittance at 430 nm of 90.0%.

Comparative Example 4

The procedure of Example 1 was repeated, except that the gas phase of the storage container was not replaced with nitrogen gas. The resulting aqueous potassium sorbate solution was stored at room temperature of 20° C. for two months and was then found to have a light transmittance at 430 nm of 92.0%.

Comparative Example 5

The procedure of Example 3 was repeated, except that the aqueous solution was stored in an atmospheric open system in which a condenser was placed to prevent the liquid level from falling due to moisture evaporation. After a lapse of four days, the resulting aqueous solution was found to have a light transmittance at 430 nm of 42.5%.

Other embodiments and variations will be obvious to those skilled in the art, and this invention is not to be limited to the specific matters stated above.

What is claimed is:

1. A method of storing an aqueous potassium sorbate solution, comprising the step of storing an aqueous potassium sorbate solution having a dissolved oxygen concentration of 3.0 mg/l or less in such a condition that the oxygen concentration of a gas phase above the liquid level of the aqueous solution is half or less than the oxygen concentration of the atmosphere, wherein said aqueous potassium sorbate solution has been prepared by degassing an aqueous potassium sorbate solution or by reducing the oxygen concentrations of a gas phase and of materials to be reacted and allowing sorbic acid to react with potassium hydroxide in the presence of water to thereby yield said aqueous potassium sorbate solution.

2. A method of storing an aqueous potassium sorbate solution, comprising the step of storing an aqueous potassium sorbate solution having a dissolved oxygen concentration of 3.0 mg/l or less in a container composed of an oxygen-impermeable material, wherein said aqueous potassium sorbate solution has been prepared by degassing an aqueous potassium sorbate solution or by reducing the oxygen concentrations of a gas phase and of materials to be reacted and allowing sorbic acid to react with potassium hydroxide in the presence of water to thereby yield said aqueous potassium sorbate solution.

* * * * *